United States Patent [19]

Weinshenker et al.

[11] Patent Number: 4,664,651
[45] Date of Patent: May 12, 1987

[54] SUBATMOSPHERIC METHOD AND APPARATUS FOR EXPANDING BLOOD VESSELS TO FACILITATE PUNCTURE WITH A CANNULA

[75] Inventors: Eugene Weinshenker; Robert S. Dirksing, both of Cincinnati, Ohio

[73] Assignee: The Procter & Gamble Company, Cincinnati, Ohio

[21] Appl. No.: 707,259

[22] Filed: Mar. 1, 1985

[51] Int. Cl.$^4$ .............................................. A61B 5/02
[52] U.S. Cl. ................... 604/115; 128/677; 128/678
[58] Field of Search .............. 128/77, 677–679; 604/115

[56] References Cited

U.S. PATENT DOCUMENTS

| | | | |
|---|---|---|---|
| 1,934,046 | 11/1933 | Demarchi | 604/115 |
| 3,101,085 | 8/1963 | Murphy, Jr. | 128/325 |
| 3,450,450 | 6/1969 | Hopkins et al. | 312/1 |
| 3,811,431 | 5/1974 | Apstein | 128/64 |
| 3,880,149 | 4/1975 | Kawaguchi | 128/24 |
| 3,885,554 | 5/1975 | Rockwell, Jr. | 128/24 |
| 3,892,229 | 7/1975 | Taylor et al. | 128/24 |
| 3,942,518 | 3/1976 | Tenteris et al. | 128/24 |
| 3,971,398 | 7/1976 | Taylor et al. | 137/119 |
| 3,976,056 | 8/1976 | Brawn | 128/24 |
| 4,007,734 | 2/1977 | Peters | 128/677 |
| 4,030,488 | 6/1977 | Hasty | 128/24 |
| 4,054,129 | 10/1977 | Byars et al. | 128/24 |
| 4,057,046 | 11/1977 | Kawaguchi | 128/24 |
| 4,153,050 | 5/1979 | Bishop et al. | 128/64 |
| 4,206,751 | 6/1980 | Schneider | 128/24 |
| 4,269,175 | 5/1981 | Dillon | 128/24 |
| 4,299,219 | 11/1981 | Norris, Jr. | 604/115 |
| 4,311,135 | 1/1982 | Brueckner et al. | 128/24 |
| 4,329,985 | 5/1982 | Bonchek | 604/115 |
| 4,353,359 | 10/1982 | Milbauer | 128/66 |
| 4,354,503 | 10/1982 | Golden | 128/677 |
| 4,374,518 | 2/1983 | Villanueva | 128/64 |
| 4,378,008 | 3/1983 | Osbon, Sr. | 128/79 |
| 4,393,870 | 7/1983 | Wagner | 604/115 |
| 4,481,937 | 11/1984 | Arkans | 128/24 |

OTHER PUBLICATIONS

An article from the *Journal of American Medical Asso.*, 10/10/35, entitled "Nonoperative Treatment of Inadequate Peripheral Distribution of Blood", by Louis G. Herrmann, M.D.

An article from the *Annals of Surgery*, vol. 100, Oct. 1934, entitled "The Conservative Treatment of Arteriosclerotic Peripheral Vascular Diseases", by Louis G. Herrmann, M.D. and Mont R. Reid, M.D.

An article from the *Archives of Surgery*, vol. 29, No. 5, Nov. 1934, entitled "Passive Vascular Exercises", by Louis G. Herrmann, M.D. and Mont R. Reid, M.D.

Chapter 31, "The Arterial System: Arteries and Arterioles", *Physiology and Biophysics*, Edited by Theodore C. Ruch, Ph.D. and Harry D. Patton, Ph.D., M.D., W. B. Saunders Company, 1965.

Primary Examiner—C. Fred Rosenbaum
Assistant Examiner—Sherri Vinyard
Attorney, Agent, or Firm—E. Kelly Linman; John V. Gorman; Richard C. Witte

[57] ABSTRACT

Method and apparatus for distending the blood vessels comprising the veins and the arteries in an isolated portion of a patient's body remote from the patient's heart to facilitate puncture with a cannula. The preferred method comprises placing the isolated portion of the patient's body within a chamber capable of supporting at least a partial vacuum and forming a substantially airtight seal between the chamber and the isolated portion of the patient's body. Venous blood flow from the isolated portion of the patient's body is then gradually restricted by circumferentially constricting the patient's body at a point approximately coinciding with the point at which the substantially airtight seal is formed. The isolated portion of the patient's body in the chamber is then subjected to a partial vacuum for a period of time sufficient for the patient's systolic arterial blood pressure to engorge the blood vessels with blood, to substantially equalize the pressure of the blood in the veins and the arteries and to substantially distend the blood vessels. Constriction of the patient's body is thereafter gradually increased until the arterial blood flow to the isolated portion substantially ceases. Finally, the vacuum chamber is vented to atmosphere and removed while the circumferential constriction is maintained to substantially prevent the flow of blood to and from the isolated portion of the patient's body. As a result, the blood vessels in the isolated portion of the patient's body are in an engorged, highly visible and highly distended condition.

31 Claims, 2 Drawing Figures

SUBATMOSPHERIC METHOD AND APPARATUS FOR EXPANDING BLOOD VESSELS TO FACILITATE PUNCTURE WITH A CANNULA

TECHNICAL FIELD

The present invention has relation to method and apparatus for increasing blood vessel distention to greatly improve visibility and access to puncture by means of a needle or cannula intended to inject material into or withdraw blood from a blood vessel.

The present invention has further relation to method and apparatus which permits easy insertion of intravenous lines for the introduction of resuscitation fluids and medications, even in a hypotensive individual.

The present invention has still further relation to method and apparatus for making the blood vessels more readily susceptible to puncture by a hypodermic needle or the like by causing the blood vessels to become engorged with blood and to assume a more round, distended condition prior to insertion of the needle.

The present invention has further relation to method and apparatus for distending blood vessels preliminary to venipuncture even in situations where arterial blood pressure falls because of dehydration, shock, cardiac insufficiency or arrest of circulation.

The present invention has further relation to compact manual apparatus for performing the foregoing operation without need for external power supplies, vacuum sources, compressed air sources, or the like.

BACKGROUND ART

Intravenous needles used for injecting or withdrawing blood, volume increasing fluids, feeding fluids, medications, blood transfusions and the like are normally inserted directly into the blood vessel by hand. Under certain pathological or traumatic conditions, particularly when blood pressure is unusually low, blood vessels lying close to the skin, such as in the arm or leg are substantially collapsed, making it difficult, if not impossible, to find the lumen upon insertion and manipulation of the needle or cannula through a skin puncture. This condition is especially critical when a patient is in shock due to excessive bleeding or internal hemorrhaging. If a licensed physician is in attendance, the emergency procedure known as a venous "cut-down" can be resorted to, exposing the vein to permit surgical cutting and direct insertion of a catheter. However, in many emergency situations in which a patient is in shock because of extensive hemorrhaging, an emergency medical technician is first to arrive at the scene to offer medical treatment. This is particularly true in the case of automobile and industrial machine accidents resulting in severe injuries to the patient. Since emergency medical technicians are normally not authorized to perform a surgical "cut-down" procedure, they must, under most such emergency conditions, use their best skills to manually insert an intravenous needle through the skin into the lumen of a vein, even though the vein is in a collapsed or partially collapsed condition due to low blood pressure. This is an extremely difficult task.

The foregoing difficulties have been recognized by a number of prior art practitioners. For example, U.S. Pat. No. 4,299,219 issued to Norris, Jr. on Nov. 10, 1981 discloses an intravenous needle insertion device having a transparent vacuum cylinder with an open end adapted for placement in sealing engagement over the skin of a patient at a zone where venipuncture is to be performed. A vacuum drawing syringe communicates with the cylinder for establishing a vacuum which serves to draw the skin and underlying vein partially into the vacuum chamber. According to the teachings of Norris, Jr., the vein will become engorged with blood to facilitate needle insertion. An intravenous needle holding and manipulating assembly is substantially coaxially arranged within the vacuum cylinder and hermetically sealed with respect thereto. The device further includes release mechanism at the open end of the vacuum cylinder for temporarily supporting an intravenous needle as well as manual grasping means at the other end to permit manipulation of the needle for insertion in the distended vein while under vacuum.

The device disclosed by Norris, Jr. et al. would, however, pose several practical difficulties in use. The first is that the medical technician would have to make an initial decision as to which vein will be entered and very precisely where the puncture is to be made, since the needle is substantially coaxially supported in the transparent vacuum cylinder. Furthermore, even if the needle of Norris, Jr. et al. were capable of slight lateral movement, the transparent cylinder would prevent the medical technician from selecting the best possible site for venipuncture after the pressure inside the chamber has been reduced, since the selection of a suitable site for venipuncture normally depends more upon palpation than visualization. In addition, since the vein selected remains within the cylinder during insertion, the medical technician is unable to manually stretch the skin (this is normally done to minimize pain), to modify the angle of attack of the needle both vertically and horizontally, to stabilize the vein with the fingers or to feel the needle actually entering the vein. Finally, the unbalanced atmospheric force resulting with the device of Norris Jr. et al. creates pressure along the edge of the cylindrical surface at the point where the seal with the patient's body is achieved. This localized force tends to clamp the veins shut if they are near the surface. To offset this clamping action created by the vacuum, it would be necessary to provide a balancing force to pull the device away from the skin to eliminate or minimize restriction of the vein. Providing such a force makes it even more difficult to manipulate entrance of the needle into the lumen of the vein.

Accordingly, it is an object of the present invention to provide method and apparatus for safely and reliably entering the blood vessel of a patient with a needle or other suitable cannula, even if the patient is suffering from hypovolemic or other forms of shock.

It is another object of the present invention to provide a multiplicity of unobstructed sites where insertion of a needle into a blood vessel is readily permitted, and the particular site to be employed can be chosen at the discretion of either the patient or the medical practitioner after the blood vessels are distended.

It is still another object of the present invention to provide method and apparatus for distending the blood vessel prior to venipuncture so that actual puncturing of the vessel by the needle is more easily facilitated.

It is still another object of the present invention to provide method and apparatus for accomplishing the foregoing objectives which are simple to apply by non-technically trained personnel, which are incapable of causing injury to the patient and which are sufficiently inexpensive that they can, if desired, be readily discarded after a single use.

DISCLOSURE OF THE PRESENT INVENTION

The present invention pertains, in a particularly preferred embodiment, to method and apparatus for providing blood vessel distention to improve access to and facilitate insertion of a hypodermic needle or other cannula into a blood vessel of the patient. The method and apparatus of the present invention provide greater blood vessel distention than the usual method of simply blocking venous return with a tourniquet, particularly when systolic pressure is low or veins are hard to find because of fat covering or damage.

In a particularly preferred embodiment, a substantially gas-impervious chamber is placed over one of the patient's limbs. An airtight seal is achieved with the patient's body at the chamber's proximal end, and pressure in the chamber is reduced to a level below atmospheric pressure. The reduced pressure to which the limb is subject allows the blood vessels in the limb to expand relative to the blood vessels in the remainder of the patient's body, which remain subject to atmospheric pressure.

A pneumatic blood pressure cuff or other constricting device, which is normally located at the proximal end of the chamber, aids in providing the airtight seal. Ideally, while the reduced pressure is maintained in the chamber, the cuff pressure is slowly increased to prevent venous return from the limb as the blood pressure in the veins rises to approach arterial pressure. This is possible because the flow restriction imposed on the veins has eliminated the normal arterial to venous pressure drop which occurs in the arterioles and precapillar sphincters when there is flow. The cuff pressure is thereafter inflated to a pressure above systolic, thus blocking any additional blood flow to or from the limb.

To maintain the maximum pressure and hence the maximum distention established in the blood vessels even after the chamber is removed, the blood pressure cuff is preferably inflated to a pressure equal to the sum (in absolute terms) of the patient's systolic arterial blood pressure plus the reduced pressure existing within the chamber prior to removal of the chamber from the patient's limb. As a result, the blood vessels of the isolated limb remain greatly distended and engorged with blood, since cuff prevents flow to or from the limb.

Once the cuff has been inflated to the desired pressure, air is thereafter admitted to the chamber to dissipate the vacuum within the chamber and the chamber is removed from the patient's limb while the cuff remains inflated. As a result of the foregoing operation, blood vessels contained in the limb are completely unobstructed by the chamber, engorged with blood, highly distended, readily visible, readily palpated and easily punctured by a hypodermic needle or cannula due to their taut condition. Once the blood vessel has been penetrated by the needle or cannula, the blood pressure cuff or other form of constricting device used to restrict blood flow to and from the limb is removed from the patient's limb to restore normal circulation.

Thus the present invention readily permits a technician, nurse or medical practitioner to quickly and accurately locate and penetrate a blood vessel at one or more sites in the limb with reduced risk of multiple unsuccessful attempts, even in patients exhibiting low blood pressure or patients having body structures which would ordinarily make this very difficult if not impossible. Accordingly the present method and apparatus may be used to great advantage not only to permit fluid resuscitation of emergency victims, but also to permit non-traumatic blood sampling and/or intravenous feeding in patients who otherwise are difficult venipuncture candidates.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

Figure 1:
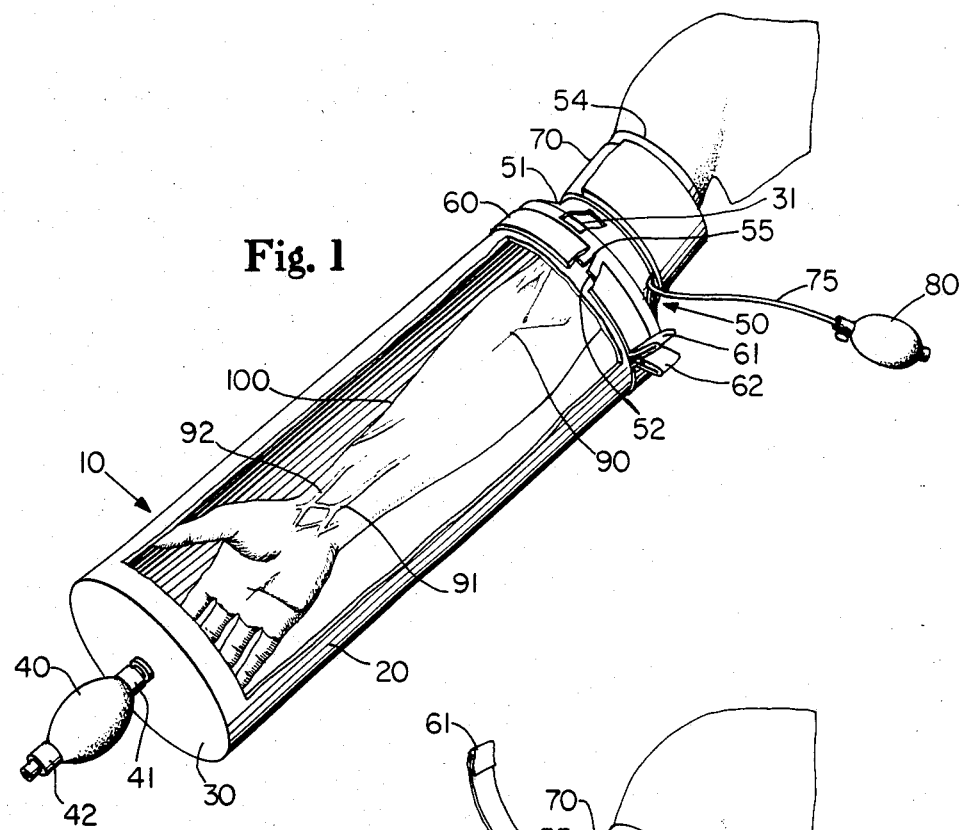
FIG. 1 is a simplified perspective illustration of a preferred apparatus of the present invention installed on the arm of a patient, a portion of said apparatus being broken away to illustrate the distention effects on the blood vessels of the patient's arm due to the subatmospheric pressure created within the chamber and the constriction of venous blood flow.

In FIG. 1 there is shown a particularly preferred embodiment of a blood vessel distention device of the present invention. The apparatus preferably comprises a vacuum chamber 10 having a closed distal end 30 and an open proximal end 31 into which the patient's limb is inserted. The chamber 10 can be comprised of substantially any material which is substantially gas impermeable and which has sufficient resistance to collapse that the subatmospheric pressures created within the chamber will not cause collapse of the chamber in use. One relatively simple and readily available material which is suitable for making a vacuum chamber 10 comprises a simple cardboard mailing tube having a metal end wall 30, the cylindrical cardboard wall surfaces 20 of which have been either wrapped or coated to make them substantially impervious to the passage of gas through the walls of the tube. The length of the cylindrical wall portion 20 of the tube is typically on the order of about 2 to about 3 feet, and its diameter is sufficiently large that it will permit insertion of the patient's limb through the orifice formed at its proximal open end 31 without substantial interference, i.e., on the order of about 5-8 inches if the device is to be applied to the patient's arm.

It will of course be recognized that although in the embodiment illustrated in FIG. 1, the chamber 10 is designed to fit the patient's arm, a larger chamber could be employed if the intended portion of the body were, for example, the leg. Similarly, a much smaller chamber could be employed if it were desirable to practice the present method invention on a smaller individual, such as a child, or on a smaller portion of the patient's body, such as the hand, etc. It is also recognized that the portion of the body selected should be one in which blood flow to and from the limb can be substantially restricted in order to retain the blood vessels which are subjected to subatmospheric pressure in a substantially distended condition once the chamber has been removed from the portion of the body subjected to the treatment. Furthermore, it will be recognized by those skilled in the art that the portion of the body to be subjected to the treatment must be remote from the patient's heart. This permits the subatmospheric pressure created within the chamber to establish a pressure differential between the treated and the untreated portions of the patient's body. This pressure differential helps to engorge the blood vessels in the portion of the body being treated. In this regard it should be noted that if the entire body of the patient were subjected to subatmospheric pressure, there would be no differential pressure to aid blood vessel distention and engorgement in a particular portion of the patient's body.

An airtight seal must be established between the proximal or open end 31 of the vacuum chamber 10 and the patient's limb, in this case the patient's arm 100. As will be observed from FIG. 1, the first end 52 of an elastomeric sleeve 50 is stretched over the outermost portion of cylindrical wall 20 of the vacuum chamber 10. It is preferably secured to the vacuum chamber 10 by means of a strip of tape 60 or similar material, the adhesive surface of which contacts both the exterior wall 20 of the vacuum chamber and the first end 52 of the elastomeric sleeve 50. As shown in FIG. 1, the band of tape 60 completely encircles the periphery of the cylindrical vacuum chamber wall 20. Upon making initial contact with one another adjacent chamber wall 20 to provide 360° securement of the sleeve 52 about the wall, each unadhered end is preferably turned upon itself so that the opposing adhesive faces of each end of the tape contact one another. This provides free ends or tabs 61,62 without exposed adhesive. Free ends 61,62 provide quick and easy access when it is desired to remove the vacuum chamber 10 from the patient's arm 100.

From the broken out section shown in FIG. 1, it will be observed that a small stress concentrating notch 55 is preferably provided in the edge of the first end 52 of the elastomeric sleeve 50. By utilizing an elastomeric sleeve 50 exhibiting a molecular orientation which permits rapid tear propagation in a direction generally parallel to the axis of the cylindrical wall 20 of the vacuum chamber 10, it is possible to readily remove the vacuum chamber simply by pulling on one or both of the free ends 61,62 of the encircling band of tape 60. As the tape 60 is peeled back from the surface of end 52 of the elastomeric sleeve and exterior wall 20 of the vacuum chamber 10, the peeling force exerted by the tape will cause the stress concentrating notch 55 to initate a tear in the elastomeric sleeve 50 in a direction generally parallel to the axis of the cylindrical vacuum chamber 10. This permits quick and easy removal of the vacuum chamber from the patient's limb while the elastomeric sleeve is, for the time being, left in place.

While nearly any elastomeric tubular member may be employed for elastomeric sleeve 50, particulaly good results have been achieved utilizing the cuff portion from a rubber glove and securing it about the periphery of the cylindrical wall 20 by means of a fiber reinforced tape, the ends of which are turned upon themselves to form a pair of adhesive-free tabls, 61,62 as generally shown in FIG. 1. The open end 54 of the elastomeric sleeve can, if desired, be rolled back about itself such that prior to use of the device, it resides in a rolled up condition at the exterior of cylindrical wall 20 near the proximal end 31 of vacuum chamber 10. This permits the medical practitioner to simply insert the vacuum chamber 10 over the limb to be treated and thereafter unroll the elastomeric sleeve 50 onto the surface of the patient's body where an airtight seal must be formed. Alternatively, an elastomeric sleeve having a relatively low-friction interior surface which can be slid up the patient's limb could be employed.

In use, the elastomeric sleeve 50 is preferably unrolled onto the patient's limb and a conventional pneumatic blood pressure cuff 70 is preferably thereafter secured about end 54 of the elastomeric sleeve 50. To ensure that a seal is established between the sleeve 50 and the patient's body, the blood pressure cuff 70 is preferably inflated by means of a conventional squeeze bulb 80 and connecting tube 75 to a pressure of about 20 millimeters of mercury. This pressure serves to not only help establish an airtight seal between the elastomeric sleeve 50 and the wearer's arm 100, but, perhaps more importantly, acts to prevent substantial axial movement of the vacuum chamber 10 in a proximal direction as the pressure inside the tube is reduced. The tendency for the chamber 10 to move up the patient's limb toward the patient's body in a proximal direction is caused by the force imbalance created on the opposing ends of the chamber. In particular, atmospheric pressure is exerted on substantially all of the distal end wall 30, while it can act only on that portion of elastomeric sleeve 50 intermediate cylindrical wall 20 and the patient's limb areas, there is a net force tending to advance the chamber 10 in a proximal direction. The blood pressure cuff 70 and elastomeric sleeve 50 prevent the force imbalance created by the subatmospheric pressure existing within the vacuum chamber 10 from pushing the entire chamber up the patient's arm, as this could cause discomfort and jamming of the closed distal end wall 30 against the patient's fingers. Alternatively, the length of chamber 10 could be increased to prevent contact with the fingers or a soft material such as resilient foam could be included inside the chamber to prevent injury if contact should occur between the foam and the patient's hand.

While it is, of course, possible to establish a subatmospheric pressure within vacuum chamber 10 by many different means well known in the art, in the embodiment illustrated in FIG. 1, a simple manually operated rubber bulb suction pump 40 is secured in the end wall 30 of the vacuum chamber, as by means of a snap-in airtight grommet (not shown). Of course any other suitable technique for establishing an airtight seal between the pump and the chamber can be employed with equal facility.

A particularly preferred rubber bulb suction pump 40 is a vacuum/pressure bulb Model No. 14-085, such as is available from Fisher Scientific of Pittsburg, Pa. The rubber bulb suction pump 40 is comprised of a resilient material and employs a pair of check valves 41, 42. The check valve 41 located on the end of the pump in fluid communication with the interior of vacuum chamber 10 is oriented so that air can be withdrawn from the interior of the chamber 10, but no air is allowed to enter in the reverse direction. Air from within the vacuum chamber 10 is withdrawn each time the resilient bulb 40 expands to its normal undeformed at rest condition. A second check valve 42 located at the opposite end of the flexible bulb 40 in fluid communication with the atmosphere exhausts the air contained within the bulb each time the bulb is manually squeezed. Check valve 42 prevents atmospheric air from reentering the bulb as the resilient bulb returns to its undeformed at rest condition, drawing with it another charge of air from vacuum chamber 10. Accordingly each complete deformation and restoration cycle of the bulb transfers a volume of air from vacuum chamber 10 substantially equal to the change in volume of the bulb when going from its deformed to its undeformed condition.

In a particularly preferred embodiment of the present invention, the pressure inside the vacuum chamber 10 is reduced to a level sufficient to accomplish the desired objective by manually compressing the resilient bulb suction pump 40 a sufficient number of times that the subatmospheric pressure created within vacuum chamber 10 is sufficient to prevent the resilient bulb portion of the pump from expanding to its undeformed at rest condition. By selecting a resilient bulb suction pump 40 which cannot return to its at rest condition when a safe yet effective subatmospheric pressure is reached inside vacuum chamber 10, injury to the patient's blood vessels and the surrounding interstitial tissues can be automatically avoided, regardless of any lack of skill in the medical practitioner.

Unlike the prior art practice using conventional rubber tourniquet techniques, the present invention permits the medical practitioner to obtain blood vessel pressures in those portions of the patient's body being treated which are actually above the patient's systolic arterial blood pressure. In particular, the maximum pressure which can be achieved in the blood vessels in that portion of the patient's body contained in the vacuum chamber 10 is equal to the sum (in absolute terms) of the patient's systolic arterial blood pressure and the vacuum pressure created within the chamber. This is particularly beneficial in treating a hypotensive individual. For example, if the systolic pressure in such an individual is only 50 millimeters of mercury, subjecting one of the patient's limbs to a vacuum pressure of 100 millimeters of mercury in accordance with the present invention would permit the medical practitioner to achieve an effective venous pressure of 150 millimeters of mercury (the absolute sum of the systolic and vacuum pressure) prior to venipuncture.

In the foregoing example, blockage of venous blood flow can be initiated either prior to establishing a partial vacuum within chamber 10 or after the desired vacuum pressure has been established within the chamber without appreciably changing the end result. If done initially it can aid in establishing the airtight seal between the chamber and the isolated portion of the patient's body as well as aid in restraining vacuum induced forces tending to move the chamber toward the patient's body.

The constriction imposed to block venous blood flow should not, however, be so great as to simultaneously block arterial blood flow until the blood vessel engorgement process has been maximized. As pointed out earlier herein, blockage of venous blood flow eliminates the normal arterial to venous pressure drop which occurs in the arterioles and precapillary sphincters when flow is present. Maximizing the engorgement of the blood vessels with blood is dependent upon a continued access to arterial blood while venous blood flow remains restricted. Since constriction of venous blood flow will occur at a much lower cuff pressure than constriction of arterial blood flow, it is generally desirable to slowly elevate the cuff pressure to maintain the restriction of venous blood flow as the venous blood pressure begins to approach the arterial blood pressure.

In the foregoing example the cuff pressure is preferably increased to a level at least approximately equal to the absolute sum of the patient's systolic arterial blood pressure plus the 100 millimeters of mercury vacuum pressure existing within the chamber 10. This latter pressure prevents the flow of blood to and from the limb even after the vacuum chamber 10 is removed. So long as this cuff pressure is maintained, the blood vessels in the isolated portion of the patient's body maintain a degree of distention corresponding to a pressure of 150 millimeters of mercury. It is for this reason that the vacuum chamber 10 is removed while the blood pressure cuff continues to restrict blood flow to and from the limb. As a result, the blood vessels, and particularly the veins, to the patient's limb are engorged with blood and distended to the same extent as though they had been subjected to a pressure of 150 millimeters of mercury at atmospheric pressure. This is normally sufficient to readily permit manual puncture with a cannula, and is in fact considerably greater than could be achieved in most normotensive individuals using prior art tourniquet techniques.

In general, greater vacuum levels will produce greater distension of the blood vessels in the limb being treated. Although subatmospheric pressures on the order of 30 millimeters of mercury will help to cause blood vessel distention experience has demonstrated that subatmospheric pressures on the order of 100 millimeters of mercury within vacuum chamber 10 are very effective in enhancing the ability of the blood vessels, e.g., blood vessels 90, 91, 92, etc., inside the limb 100 to elastically distend and become engorged with blood.

While not wishing to be bound, it is believed that during the engorgement process the veins temporarily expand from a relatively flat cross-section to a more cylindrical cross-section of much greater flow area. This not only makes them easier to locate, but also easier to penetrate due to their taut condition. In this regard, it will be appreciated that since arteries are normally at higher pressure and more cylindrical in cross-section, application of the present blood vessel engorgement and distention method to an isolated portion of the patient's body will normally produce more noticeable distention of the veins than the arteries in the limb being treated.

As pointed out with respect to the example described earlier herein, after the desired subatmospheric pressure level has been established within vacuum chamber 10, the air pressure in the pneumatically operated blood pressure cuff 70 is slowly increased to an ultimate level approximately equal to the sum (in absolute terms) of the patient's systolic arterial blood pressure plus the vacuum pressure existing within chamber 10 by means of resilient squeeze bulb 80 and connecting tube 75. Although cuff pressures just above systolic are normally sufficient to block arterial and venous flow to or from the patient's limb 100, it is generally preferred in the practice of the present invention to elevate the cuff pressure to a level approximating the absolute sum of the patient's systolic arterial blood pressure and the vacuum pressure existing within chamber 10. This prevents leakdown of the blood vessels in the treated limb from a fully distended condition upon venting of the vacuum chamber. For most patients this equates to maximum cuff inflation pressures in the range of 200-250 millimeters of mercury or less.

As described earlier herein, it is necessary that the blood pressure cuff 70 remain inflated to constrict blood flow when the vacuum chamber 10 is vented and removed from the patient's limb. This is preferably accomplished by pulling on one or both of the free tabs 61, 62 of the band of encircling tape 60 which secures end 52 of the elastomeric sleeve 50 about the perimeter of the cylindrical wall 20 of the vacuum chamber.

When the band of tape is stripped from the cylindrical wall 20 and the end 52 of the elastomeric sleeve 50, it encounters the stress concentrating notch 55 in end 52 of the elastomeric sleeve. Forces exerted by removal of the tape band 60 cause the stress concentrating notch 55 to propagate a tear in a direction generally parallel to the axis of the cylindrical vacuum chamber 10 due to the molecular orientation of the sleeve. This greatly simplifies and accelerates the process of removing the chamber 10 from the patient's limb without disturbing the inflated cuff.

Figure 2:
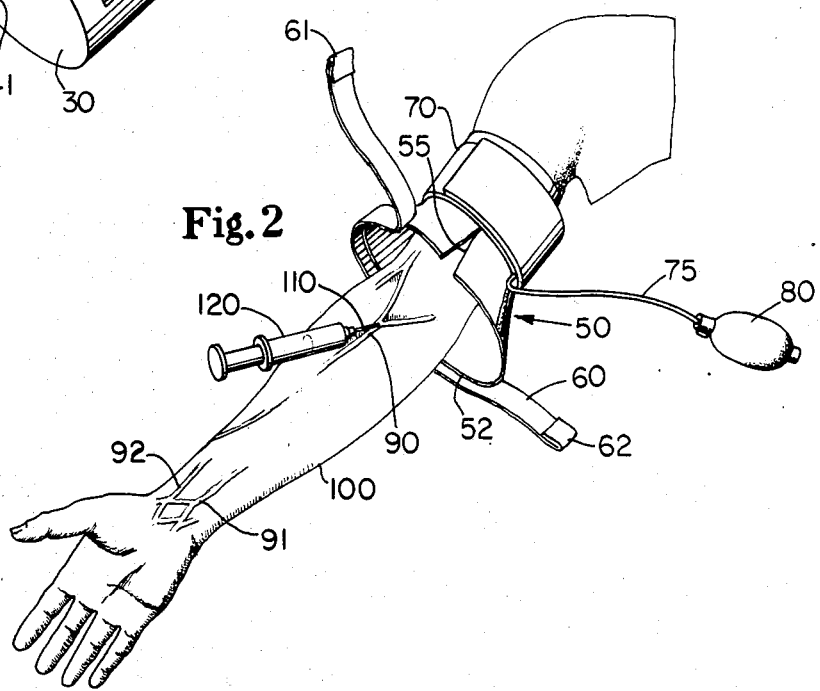
FIG. 2 is an illustration generally similar to that of FIG. 1, but illustrating the condition of a patient's arm after the blood pressure cuff has been inflated to restrict flood flow to and from the patient's arm and after the vacuum chamber has been removed, one of the blood vessels in the patient's arm having been penetrated by the needle of a hypodermic syringe.

After the vacuum chamber 10 is removed, the patient's arm is in the condition generally illustrated in FIG. 2, i.e., blood vessels such as 90, 91, 92, etc., are in a greatly distended condition and are engorged with blood with is prevented from escaping due to the restriction imposed on the patient's limb by the inflated blood pressure cuff 70. Accordingly, it is possible for either the patient or the medical practitioner to select any particular blood vessel desired to insert a cannula or needle such as the needle 110 on hypodermic syringe 120 for the purpose of injecting fluid or withdrawing blood. Because insertion of the needle 110 occurs while the readily visible blood vessel 90 (assuming this is the particular blood vessel selected) is in a distended, engorged and substantially taut condition, penetration of the blood vessel by the needle is relatively easier when contrasted to insertion of such a needle in a blood vessel which has not been subjected to the distention method of the present invention. Once the needle 110 has penetrated the blood vessel selected, the blood pressure cuff 70 can be deflated and removed from the patient's arm 100 without disturbing the inserted needle. Once the blood pressure cuff 70 is removed, the tear initiated in the elastomeric sleeve is preferably extended so as to longitudinally sever the elastomeric sleeve 50, thereby facilitating its removal from the patient's limb, also without disturbing the inserted needle. This removal technique is particularly desirable in situations where intravenous fluid tubing or the like has been connected to the needle or cannula inserted into the blood vessel.

Release of the blood pressure cuff 70 allows reestablishment of unrestricted blood circulation to and from the limb so that the blood vessels in the limb rapidly return to their normal, non-distended, non-engorged condition.

While the method described in connection with the examples shown in FIGS. 1 and 2 is particularly preferred, an alternate approach for using the apparatus shown in FIG. 1 to even further distend the blood vessels in the limb to be treated would be to establish the desired vacuum level within chamber 10, increase the pressure in the pneumatic blood pressure cuff 70 to slightly above systolic, maintaining it for about 15 seconds or move to cause ischemia in the total limb contained within the vacuum chamber 10, thereafter reducing the pressure in the cuff to a lower value to permit return of circulation and then proceeding as previously described. As a result of hormonal products released by the body in response to this hypoxia, a rebound hyperemia is established as the blood vessels in the limb being treated dilate. This causes an additional volume of blood to enter the limb. By carrying out this operation while the desired vacuum level is present within chamber 10, the blood vessels contained within the limb being treated will be even further engorged and distended when the blood pressure cuff is again slowly pressurized to restrict blood flow to and from the limb.

The basic hyperemic reaction, which may be desirable in some particularly difficult patients, is discussed in greater detail in THE ARTERIAL SYSTEM: ARTERIES AND ARTERIOLES, Chapter 31, of the book *PHYSIOLOGY AND BIOPHYSICS*, Theodore C. Ruch, Editor, W. B. Saunders Co., Philadelpha, published in 1965, said text being hereby incorporated herein by reference.

As will be appreciated by those skilled in the art, the apparatus utilized to perform the blood vessel distention operation described herein may vary substantially in configuration and appearance. For example, a vent valve could be added to the vacuum chamber to facilitate venting without removal of the elastomeric sleeve. In addition, the rubber bulb suction pump which, in a preferred embodiment, is selected so as to avoid the possibility of creating an excessive level of vacuum within chamber 10, could be replaced by a spring loaded bellows and a pair of check valves formed integrally therewith or added thereto. Alternatively, a more conventional source of vacuum used in conjunction with a safety relief valve to prevent excessive vacuum pressures from being developed within the vacuum chamber could also be employed.

Although in general, higher vacuum levels in chamber 10 will produce greater distention of the blood vessels in the limb being treated, subatmospheric pressures on the order of 100 millimeters of mercury are believed quite effective in causing the blood vessels inside the limb being treated to distend substantially and become engorged with blood. To prevent injury to either the patient's body vessels or the interstitial tissues surrounding the blood vessels excessively high vacuum pressures should not be developed within the chamber. In this regard, it should be noted that the teachings of the prior art (see particularly U.S. Pat. No. 4,329,985 issued to Bonchek on May 18, 1982 and hereby incorporated herein by reference) suggest that distention of human veins at pressures in excess of 500 millimeters of mercury can damage the vascular endothelium. Since little is presently known about the possible effect of extremely high vacuum pressures on the interstitial tissues surrounding the blood vessels, the upper level of vacuum pressure is preferably limited to the lowest practical value which will afford the engorgement and distention benefits of the present invention without risking injury to the patient.

To minimize any chance of misuse or injury to the patient, the method and apparatus for the present invention should be utilized only under the direction of or in accordance with a protocol established by a licensed medical practitioner who it totally familiar with the limits and operating parameters of the particular system to be employed.

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A method for distending the blood vessels comprising the veins and the arteries in an isolated portion of a patient's body remote from the patient's heart and thereafter puncturing one or more of said vessels with a cannula, said method comprising the steps of:

(a) placing said isolated portion of the patient's body within a chamber capable of supporting at least a partial vacuum;

(b) forming a substantially airtight seal between said chamber and said isolated portion of the patient's body;

(c) restricting the venous blood flow from said isolated portion of the patient's body by circumferentially constricting the patient's body at a point approximately coinciding with the point at which said substantially airtight seal is formed between said vacuum chamber and said isolated portion of the patient's body until said venous blood flow from said isolated portion of the patient's body substantially ceases;

(d) subjecting said isolated portion of the patient's body to a partial vacuum within said chamber for a period of time sufficient for the patient's systolic arterial blood pressure to engorge the blood vessels contained within said isolated portion of the patient's body with blood, to substantially equalize the pressure of the blood in the veins and the arteries and to substantially distend said blood vessels;

(e) gradually increasing said constriction of the patient's body until the arterial blood flow to said isolated portion of the patient's body substantially ceases;

(f) venting said chamber to atmosphere and thereafter removing said chamber from said isolated portion of the patient's body while circumferentially constricting said isolated portion of the patient's body to a degree sufficient to substantially prevent the flow of blood to and from said isolated portion of the patient's body, whereby the blood vessels in said isolated portion of the patient's body are in an engorged, highly visible and highly distended condition; and (g) inserting a cannula into one of said engorged, highly visible and highly distended blood vessels in said isolated portion of the patient's body and thereafter releasing said circumferential constriction of the patient's body to restore normal blood circulation to and from said isolated portion of the patient's body.

2. The method of claim 1, wherein said circumferential constriction of the patient's body is ultimately applied at a pressure substantially equal to the absolute sum of the patient's systolic arterial blood pressure plus the partial vacuum pressure existing within said chamber prior to venting thereof.

3. The method of claim 1, wherein said substantially airtight seal between said chamber and said isolated portion of the patient's body is established by securing a first end of a substantially air impervious elastomeric sleeve about the perimeter of the proximal end of said chamber and the second end of said elastomeric sleeve about the perimeter of said isolated portion of the patient's body.

4. The method of claim 1, wherein said partial vacuum within said chamber is created by actuating a manual suction pump which is in fluid communication with the interior of said chamber.

5. The method of claim 1, wherein a partial vacuum pressure of at least about 30 millimeters of mercury is created within said chamber.

6. The method of claim 3, wherein said circumferential constriction of the patient's body is applied over said second end of said elastomeric sleeve which contacts the patient's body.

7. The method of claim 6, wherein said chamber is removed from said isolated portion of the patient's body without disturbing said circumferential constriction of the patient's body of stripping said first end of said elastomeric sleeve from said chamber and thereafter removing said chamber.

8. The method of claim 1, wherein said isolated portion of the patient's body comprises one of the patient's limbs.

9. The method of claim 1, including the step of withdrawing blood from the blood vessel into which said cannula has been inserted.

10. The method of claim 1, including the step of injecting fluid into the blood vessel into which said cannula has been inserted.

11. The method of claim 1, wherein said partial vacuum is created within said chamber prior to restricting the venous blood flow from said isolated portion of the patient's body.

12. The method of claim 1, wherein vacuum induced movement of said chamber toward the patient's body is resisted by the means used to establish said airtight seal between the patient's body and said chamber.

13. A method for distending the blood vessels comprising the veins and arteries in an isolated portion of a patient's body remote from the patient's heart and thereafter puncturing one or more of said vessels with a cannula, said method comprising the steps of:

(a) placing said isolated portion of the patient's body within a chamber capable of supporting at least a partial vacuum;

(b) forming a substantially airtight seal between said chamber and said isolated portion of the patient's body;

(c) evacuating sufficient air from within said chamber to create a partial vacuum within said chamber;

(d) restricting the venous blood flow from and the arterial blood flow to said isolated portion of the patient's body by circumferentially constricting the patient's body at a point approximately coinciding the point at which said airtight seal is formed between said vacuum chamber and said isolated portion of the patient's body by applying a circumferential constriction pressure at least equal to the patient's systolic arterial blood pressure for a period of at least about 15 seconds;

(e) reducing said circumferential constriction pressure sufficiently to permit restoration of arterial blood flow to and venous blood flow from said isolated portion of the patient's body while maintaining said partial vacuum in said chamber, thereby enabling the establishment of a rebound hyperemia in said isolated portion of the patient's body;

(f) again restricting the venous blood flow from said isolated portion of the patient's body while said rebound hyperemia is present by circumferentially constricting the patient's body at a point approximately coinciding with the point at which said substantially airtight seal is formed between said vacuum chamber and said isolated portion of the patient's body until said venous blood flow from said isolated portion of the patient's body substantially ceases, thereby allowing the patient's systolic aeterial blood pressure to engorge the blood vessels contained within the isolated portion of the patient's body with blood, to substantially equalize the pressure of the blood in the veins and the arteries and to substantially distend said blood vessels;

(g) gradually increasing said constriction of the patient's body until the arterial blood flow to said isolated portion of the patient's body substantially ceases;

(h) venting said chamber to atmosphere and thereafter removing said chamber from said isolated portion of the patient's body while circumferentially constricting said isolated portion of the patient's body to a degree sufficient to substantially prevent the flow of blood to and from said isolated portion of the patient's body, whereby the blood vessels in said isolated portion of the patient's body are in an engorged, highly visible and highly distended condition; and (i) inserting a cannula into one of said engorged, highly visible and highly distended blood vessels in said isolated portion of the patient's body and thereafter releasing said circumferential constriction of the patient's body to restore normal blood circulation to and from said isolated portion of the patient's body.

14. The method of claim 13, wherein said second circumferential constriction of the patient's body is ultimately applied at a pressure substantially equal to the absolute sum of the patient's systolic blood pressure plus the partial vacuum pressure existing within said chamber prior to venting thereof.

15. The method of claim 13, wherein sufficient air is evacuated from said chamber to establish a partial vacuum pressure of at least about 30 millimeters of mercury within said chamber.

16. The method of claim 13, wherein said isolated portion of the patient's body comprises one of the patient's limbs.

17. The method of claim 13, including the step of withdrawing blood from the blood vessel into which said cannula has been inserted.

18. The method of claim 13, including the step of injecting fluid into the blood vessel into which said cannula has been inserted.

19. Apparatus for distending the blood vessels in an isolated portion of a patient's body remote from the patient's heart and for puncturing one or more of said vessels, said apparatus comprising in combination:

(a) a closed chamber comprised of substantially air impervious material and having an orifice at its proximal end for insertion of said isolated portion of the patient's body, said chamber being capable of supporting at least a partial vacuum;

(b) means for forming a substantially airtight seal between said orifice in said chamber and said isolated portion of the patient's body;

(c) means for evacuating air from within said chamber to create a partial vacuum within said chamber;

(d) means for gradually restricting the flow of blood to and from said isolated portion of the patient's body by circumferentially constricting said isolated portion of the patient's body contained within said chamber until said flow of blood to and from said isolated portion of the patient's body substantially ceases, said means being located at a point substantially coinciding with the point at which said substantially airtight seal is formed between said vacuum chamber and said isolated portion of the patient's body;

(e) means for venting said chamber and thereafter removing said chamber from said portion of the patient's body while continuing to circumferentially constrict the patient's body to a degree sufficient to substantially prevent the flow of blood to and from said portion of the patient's body; and (f) cannulation means for puncturing one or more of said distended blood vessels in said isolated portion of the patient's body.

20. The apparatus of claim 19, wherein said means for forming a substantially airtight seal between said orifice at the proximal end of said chamber and said isolated portion of the patient's body comprises a substantially air impervious elastomeric sleeve having a first end sealingly secured about the perimeter of said orifice and a second end which forms an elastic seal about the perimeter of said isolated portion of the patient's body.

21. The apparatus of claim 20, wherein said means for restricting the flow of blood to and from said isolated portion of the patient's body comprises a pneumatically actuated pressure cuff.

22. The apparatus of claim 21, wherein said pressure cuff is applied over said second end of said elastomeric sleeve, thereby enhancing the airtight seal formed between said second end of said elastomeric sleeve and said isolated portion of the patient's body as well as resisting the imbalanced atmospheric forces acting on the vacuum chamber which tend to cause movement of the vacuum chamber toward the patient's body.

23. The apparatus of claim 22, wherein said first end of said elastomeric sleeve is releasably secured about the perimeter of said orifice in said chamber to permit removal of said chamber from the patient's body without removal of said elastomeric sleeve.

24. The apparatus of claim 23, wherein said elastomeric sleeve is molecularly oriented in a direction generally parallel to its length, said first end of said sleeve including a stress concentrating feature which initiates a self-propagating tear generally parallel to the length of said sleeve when said first end of said sleeve is removed from the perimeter of said orifice at the proximal end of said chamber.

25. The apparatus of claim 19, wherein said means for evacuating air from said chamber comprises a manually operated suction pump in fluid communication with said chamber.

26. The apparatus of claim 25, wherein said manually operated suction pump includes safety means to limit the level of vacuum which can be achieved in said chamber to a pressure which is insufficient to cause injury to either the blood vessels or the surrounding interstitial tissues in said isolated portion of the patient's body.

27. The apparatus of claim 26, wherein said manually operated suction pump comprises a resiliently deformable bulb, said bulb including a first check valve in fluid communication with said chamber and a second check valve in fluid communication with the atmosphere, said safety means comprising the inability of the wall portion of said resiliently deformable bulb to return to its undeformed at rest condition before a vacuum pressure sufficient to cause injury to said isolated portion of the patient's body is produced in said chamber.

28. The apparatus of claim 20, wherein said means for venting said chamber comprises said elastomeric sleeve.

29. The apparatus of claim 20, wherein said means for venting said chamber comprises a valve in fluid communication with said chamber.

30. The apparatus of claim 19, wherein said chamber comprises a cylindrical member having a closed distal end, said orifice in said chamber comprising an open end of said cylindrical member.

31. The apparatus of claim 30, wherein said cylindrical member is rigidly secured to a substrate to prevent vacuum induced axial movement thereof toward the patient's body.

* * * * *

UNITED STATES PATENT AND TRADEMARK OFFICE
CERTIFICATE OF CORRECTION

PATENT NO. : 4,664,651

DATED : May 12, 1987

INVENTOR(S) : Eugene Weinshenker and Robert S. Dirksing

It is certified that error appears in the above-identified patent and that said Letters Patent is hereby corrected as shown below:

Column 3, line 32, "precapillar" should read -- precapillary --.

Column 4, line 22, "flood" should read -- blood --.

Column 5, line 53, "particulaly" should read -- particularly --.

Column 5, line 58, "tabls," should read -- tabs, --.

Column 7, line 36, "pressure)" should read -- pressures) --.

Column 8, line 21, after "distention" insert -- , --.

Column 8, line 24, "ehancing" should read -- enhancing --.

Column 9, line 16, "with" should read -- which --.

Column 10, line 53, "it" should read -- is --.

Column 12, line 6, "of" should read -- by --.

Signed and Sealed this

First Day of September, 1987

Attest:

DONALD J. QUIGG

Attesting Officer

Commissioner of Patents and Trademarks